United States Patent [19]

Smith

[11] Plant 4,560

[45] Jul. 1, 1980

[54] MYOPORUM PLANT

[76] Inventor: George C. Smith, 436 Greenwood, Arroyo Grande, Calif. 93420

[21] Appl. No.: 20,878

[22] Filed: Mar. 15, 1979

[51] Int. Cl.[2] ..... A01H 5/00

[52] U.S. Cl. ..... Plt./54

[58] Field of Search ..... Plt./54

*Primary Examiner*—Robert E. Bagwill

*Attorney, Agent, or Firm*—Vincent G. Gioia

[57] ABSTRACT

A new and distinct Myoporum plant discovered in San Luis Obispo County, Calif., having a unique growth habit.

1 Drawing Figure

The present invention relates to a new and distinct variety of Myoporum plant which was discovered in Arroyo Grande, Calif., San Luis Obispo county.

There are two commonly known Myoporum species in the trade. Each is distinctly different from my plant. Myoporum laetum is a large spreading, globe-shaped shrub or small tree. It grows to a height of 30-feet with a spread of 20-feet. Its leaves are 3 to 4-inches long and approximately 1-inch wide. Myoporum parvifolium is an almost viney, low growing groundcover which grows to a height of a few inches with a spread of 9-feet. Its leaves are ⅛ to ¼-inch wide and about 1-inch long.

My new Myoporum combines characteristics of both of the above. It is a woody plant, prostrate in form, with a height of 12 to 18-inches and a spread of 12 to 15-feet. Its leaves are ½ to ¾-inches wide and 2 to 3-inches long.

Among the novel characteristics possessed by this new variety which distinguish it from other varieties of which I am aware are: (1) a woody plant prostrate in form attaining a height of 12 to 18-inches and a spread of 12 to 15-feet with leaves ½ to ¾-inches wide and 2 to 3-inches long, (2) winter hardiness evidenced by survival through at least 20° F., (3) tolerant of coastal conditions growing well in sandy soil at cool temperatures and substantial moisture and (4) vigorous growing ability tolerating pruning and shaping in any season. Asexual reproduction of the new variety by soft wood cuttings as performe- in San Luis Obispo county, Calif., shows that the foregoing and other distinguishing characteristics come true to form and are established through succeeding propagations.

The accompanying drawing shows typical specimens of vegetative growth of the new variety depicted in color as nearly true as it is reasonably possible to make the same in a color illustration of this character.

The following observations and descriptions of the new variety of Myoporum were made of specimens grown outdoors in San Luis Obispo county, Calif., in the month of July. The description uses customary horticultural terminology and where color plate numbers are referred to, the reference is to Royal Horticultural Society Color Chart (RHSCC) and color plate numbers thereof, e.g., "147A" refers to plate 147A of the RHSCC yellow green group.

PLANT

General growth habit: Vigorous growing, well branched, dense with stiff branches.

Typical dimensions:

*Height.*—17.7 inches.

*Spread.*—13.2 feet.

Foliage: Leaf description — simple, elliptic to 2.6-3.5 inches long, about one inch wide; tip acute; base attenuate; petiole much reduced to leaves sessile; margin upper ⅔ serrate to lower ⅓ entire.

*Quantity.*—Leaves numerous overall; one leaf per node, alternate.

*Color.*—Mature leaf, top 147A and underside 146A — immature leaf, top 137A and underside 138B.

*Texture.*—Leaves thick; upper surface shiny; lower surface rough darker green, bumpy due to pronounced clear gland-like structures in the leaves. Younger leaves are a bit softer but general texture for young and old leaves are as described.

*Aspect.*—Midvein raised and pronounced on the lower surface with raised bumps, as described above, being clear and gland-like when held to a light. Leaves slightly reflexed back toward the stem. Upper surface slightly folded upward.

*Rooting.*—Fibrous, shallow, prolific, aggressive.

*Disease and insect resistance.*—No apparent insect or disease problems.

FLOWERS

Blooming habit: Flowers are in clusters of three and four in axils of the leaves. Solitary flowers are on stalks 0.24 to .04 inch long; old flowers are persistent.

Blooming season: Sporadic bloom throughout year — main season is late spring and summer.

Flower: Perfect, calyx 6, corolla 5, lobed sympetalous, somewhat rotate, 6 mm. long, 10 mm. wide. Corolla white at times with purplish spots especially near the base. White hairs on upper surface, setaceous.

Reproductive organs:

*Stigma.*—Slender 7 mm. long, not knob-like, tan to brown with age.

*Stamens.*—4, inverted on corolla slightly exerted, 5 mm. long, light tan to brown, smooth and elliptic in cross section.

*Anthers.*—Inverted "V" shaped on filament, versatile, light brown.

Fruit: A drupe, dark purple to black, 7 to 9 mm. long, 5 to 6 mm. wide. All observed were one-seeded.

The new variety of Myoporum which I have discovered is very well suited for use as ground cover on banks or flat areas. It is also very useful for erosion control and traffic control because of its rigid branch structure.

I claim:

1. A new and distinct variety of Myoporum plant discovered in a cultivated area, substantially as shown and described, characterized particularly by a distinctive woody plant prostrate in form attaining a height of 12 to 18-inches and a spread of 12 to 15-feet, leaves ½ to ¾-inches wide and 2 to 3-inches long and dense growing ability making it especially useful for erosion and traffic control and of tolerance for pruning and shaping in any season.

* * * * *

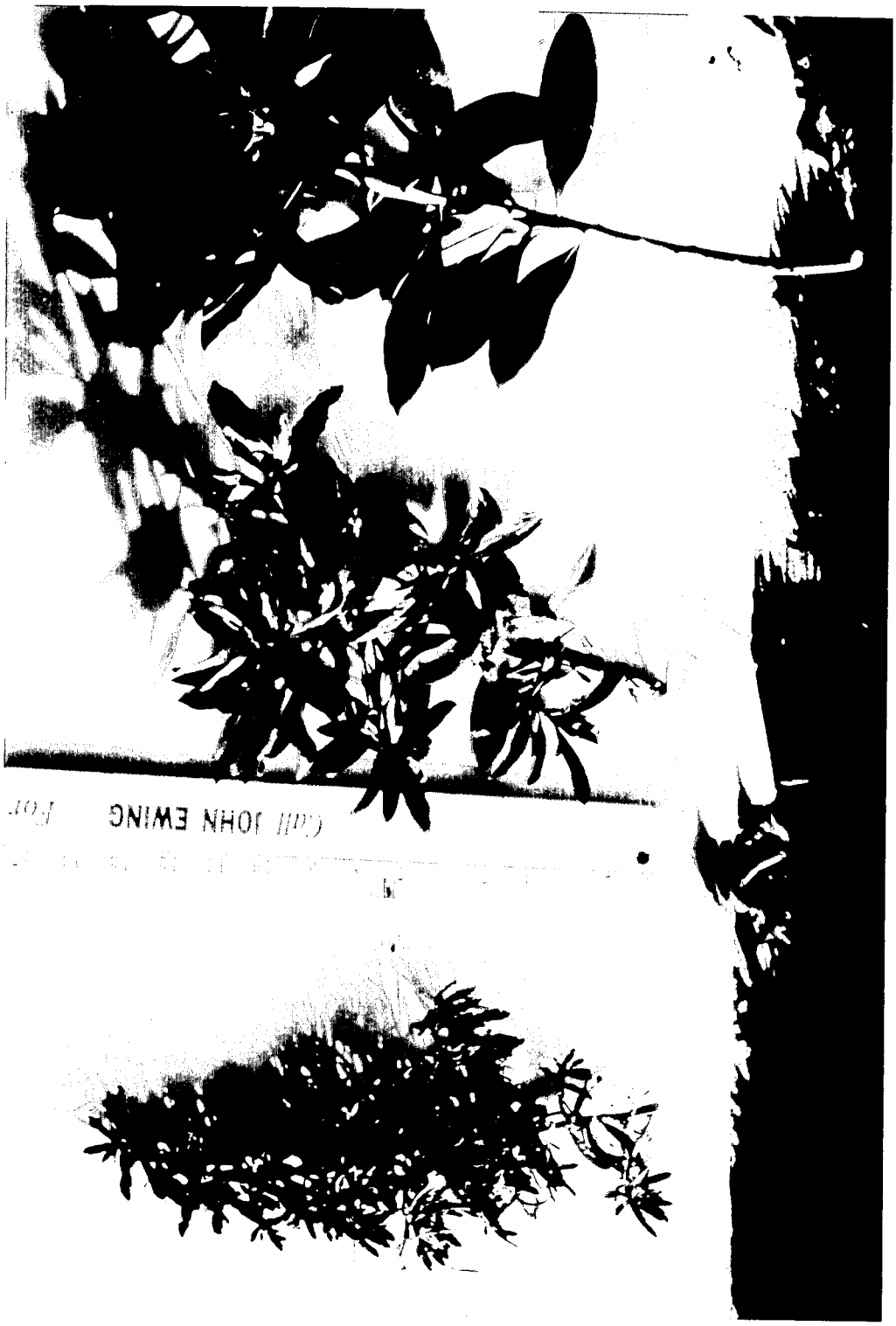
JOHN EWING